United States Patent [19]

Sheth

[11] Patent Number: 4,793,999

[45] Date of Patent: Dec. 27, 1988

[54] METHOD OF MANUFACTURING AN ANTIHYPERTENSIVE, DIURETIC AND ANTIHYPOKALEMIC PHARMACEUTICAL COMPOSITION WITH POLYETHYLENE GLYCOL

[76] Inventor: Prabhakar R. Sheth, 224 Highland Ave., Pearl River, N.Y. 10965

[21] Appl. No.: 30,559

[22] Filed: Mar. 27, 1987

[51] Int. Cl.[4] .............................................. A61K 31/74
[52] U.S. Cl. ................................... 424/451; 424/464; 424/78; 514/223.5
[58] Field of Search ............................... 514/222, 225

[56] References Cited

U.S. PATENT DOCUMENTS

| | | | |
|---|---|---|---|
| 3,163,576 | 12/1964 | Havemeyer | 514/225 |
| 4,255,413 | 3/1981 | Rattle et al. | 424/37 |
| 4,425,345 | 1/1984 | Horlington et al. | 514/249 |
| 4,444,769 | 4/1984 | Blume et al. | 424/24 B |

FOREIGN PATENT DOCUMENTS

EP131950 1/1985 European Pat. Off. .
2502952 10/1982 France .

OTHER PUBLICATIONS

A. V. Deshpande and D. K. Agarwal, "Increasing the Dissolution Rate of Some Benzothiadiazine Derivatives by Solid & Liquid Dispersion Techniques", 8(6) 1982, Drug Development & Industrial Pharmacy, pp. 883–897.

J. K. Pandit & B. K. Khakurel, "In Vitro & In Vivo Evaluation of Some Fast Release Dosage Forms of Hydrochlorthiazide", Oct. 10, 1984, Drug Development & Industrial Pharmacy, pp. 1709–1724.

M. A. Kaslem et al., "On the Dissolution of Hydrochlorthiazide Powders and Solid Dispersions", 44, No. 11, 1982, Pharm. Ind., pp. 1186–1189.

Primary Examiner—Joseph L. Schofer
Assistant Examiner—Peter F. Kulkosky

[57] ABSTRACT

A novel method of manufacturing a novel effective antihypertensive, diuretic and antihypokalemic pharmaceutical composition in which a triamterene active pteridine, a hydrochlorothiazide active benzothiadiazide, and a filler are thoroughly mixed with a polyethylene glycol, applying heat to the melting point thereof when the mixture instantaneously fuses to form granules, while cooled, then the granules are formulated into effective dosage units.

12 Claims, No Drawings

4,793,999

METHOD OF MANUFACTURING AN ANTIHYPERTENSIVE, DIURETIC AND ANTIHYPOKALEMIC PHARMACEUTICAL COMPOSITION WITH POLYETHYLENE GLYCOL

FIELD OF THE INVENTION

This invention relates to a novel method of manufacturing a novel effective antihypertensive, diuretic, antihypokalemic pharmaceutical composition in which a triamterene active pteridine, a hydrochlorothiazide active benzothiadiazide and a filler are thoroughly mixed with polyethylene glycol while heating to its melting point to fuse the constituents into granules while cooling, which are then mixed with pharmaceutically acceptable inert ingredients and a lubricant and formed into effective dosage units.

PRIOR ART

Hydrochlorothiazide (HCT) has been known to be a useful diuretic and to reduce hypertension. However, when administered alone to a patient, it can result in a loss of potassium or a condition known as hypokalemia. In order to counteract the loss of potassium, it is therefore usually administered with a pteridine such as triamterene (TT). This has been described in U.S. Pat. No. 3,081,230, Weinstock et al., issued Mar. 12, 1963; by Kobuckka et al., 205 Acta Med Scand Vol. 205, pages 319–324 (1979) and "The Influence of Dosage Form on the Activity of a Diuretic Agent" by Tannenbaum et al., Clinical Pharmacology and Therapeutics, Vol. 9, No. 5, pp 598–604 (1968), as described in Blume et al., in U.S. Pat. No. 4,444,769, issued Apr. 24, 1984, which is incorporated herein by reference. Typically, such prior art compositions have been prepared by intimately mixing the HCT and TT together with suitable fillers and forming the mixture into dosage units.

One of the problems arising from the use of such mixtures is that the components have been only erratically and incompletely absorbed into the system of patients because of poor dissolution in gastric juices and, thus, have provided only low bioavailability of the active components.

In an effort to overcome this and other problems associated with intimate mixtures of HCT and TT, it has been proposed as described in U.S. Pat. No. 4,444,769, Blume et al., supra, to form separate granulations, one of finely divided TT mixed with at least one pharmaceutically inert ingredient, and another of finely divided HCT mixed with at least one pharmaceutically inert ingredient. The separate granules are then admixed and blended together so that the resulting blended compositions has a weight ratio of the TT to the HCT which provides an effective bioavailability of the TT to control the hypokalemic condition induced by the dosage amount of the HCT. This weight ratio is preferably 1.5:1 which was known to be most clinically effective. In so doing, when the HCT and TT is granulated separately, Blume et al. found that this increased the solubility and bioavailability of the TT and accordingly reduced the hypokalemic side effects of the HCT.

In an attempt to avoid the cumbersome steps of forming separate granules before combining finely divided TT and HCT, it was recognized that polyethylene glycol (PEG) has been used as a carrier or solvent for pharmaceutical components. However, in view of Blume et al. in U.S. Pat. No. 4,444,769, it was considered inappropriate to attempt to use PEG as a carrier because if the HCT and TT were combined intimately with the PEG, it was believed that the product would have poor dissolution and subsequent reduced bioavailability of the TT.

Quite unexpectedly it was found that if certain precautions are followed, a pharmaceutical composition with intimately mixed TT and HCT in an effective weight ratio, granulated in a special manner, using a PEG as the granulating agent, not only does it not have reduced dissolution of the TT, but actually possesses increased dissolution in gastric juice, indicative of its bioavailability when administered to a patient.

SUMMARY OF THE INVENTION

The present invention provides a pharmaceutical composition and associated methods, having diuretic and antihypertensive activity while inhibiting hypokalemic side effects, containing a triamterene ingredient and a hydrochlorothiazide ingredient in the desired dosage unit form, with a minimum effective amount of triamterene and having enhanced bioavailability of both ingredients in virtue of enhanced dissolution and subsequent uniform absorption of these ingredients in a patient.

In accordance with this invention, the present composition is made by simply introducing a mixture of HCT, TT and an inert filler or fillers into a polyethylene glycol, of molecular weight of about 3350–20,000, raised to its melting point to fuse the mixture and allowed to cool to form granules composed of polyethylene glycol, TT, HCT and the filler, or fillers. These granules are then mixed with a lubricant and formed into dosage units. Other acceptable pharmaceutical ingredients are usually added as known in the tabletting and encapsulation art to prepare the dosage unit.

Further, in accordance with the invention, the TT, HCT and filler components can either be first mixed and then quickly introduced into the vigorously mixed PEG which has been heated to its melting point with the rapid formation of granules, while cooling, or the TT, HCT, filler and PEG can be mixed or blended followed by bringing the PEG to its melting point while vigorously mixing to form the granules while cooling.

In either case, the PEG is heated to its melting point only long enough to fuse the constituents, i.e. almost instantaneously, and then cooled to form granules consisting of the components in a PEG matrix in the desired proportion.

An object of this invention is to provide a method of manufacturing an antihypertensive, diuretic, antihypokalemic composition in which HCT, TT and suitable filler components are combined in a single granulation with a PEG.

A further object of the invention is to provide a pharmaceutical composition having combined pharmaceutically-effective antihypertensive, diuretic and antihypokalemic properties in a single unit dosage form with improved dissolution of the active ingredients, indicative of better bioavailability.

Another object of this invention is to provide a pharmaceutical composition having combined pharmaceutically-effective antihypertensive, diuretic and antihypokalemic properties composed of a hydrochlorothiazide-active benzothiadiazide ingredient and a triamterene-active pteridine ingredient, combined in a carrier of polyethylene glycol having improved dissolution and thus effective bioavailability of the pteridine ingredient in minimum dosage.

A still further object of this invention is to provide a pharmaceutical composition having combined pharmaceutically-effective antihypertensive, diuretic and antihypokalemic properties in a single unit dosage form without separately compounding the finely divided active ingredients.

Another object of the present invention is to provide a simple method of manufacture of a composition containing triamterene and hydrochlorothiazide in an effective dosage unit form employing a minimal amount of triamterene.

These and other objects will become apparent from the following description and appended examples.

DESCRIPTION OF THE PREFERRED EMBODIMENTS

In a preferred embodiment of this invention, quantities of the triamterene ingredient and hydrochlorothiazide ingredient to render a weight ratio of about 75:50, respectively, for best results, are mixed or blended with about 5-25% by weight of polyethylene glycol, about 16% being preferred, based on the active ingredients. Other inert pharmaceutically acceptable ingredients such as lactose filler and sodium starch glycolate disintegrant are added. This mixture is then heated to the melting point of the PEG with stirring only long enough for the components to fuse, i.e. almost instantaneously, to form granules of PEG containing TT, HCT and pharmaceutically acceptable ingredients, while cooling.

Alternatively, the HCT, TT, disintegrant and filler can be premixed or blended and then rapidly introduced into the PEG which is heated to its melting point, while mixing, only long enough to receive the premixed constituents and to fuse with those constituents and form granules.

As soon as the constituents have fused with the PEG, which is almost instantaneous and the fused composition is cooled, the resulting granules are mixed with various pharmaceutically acceptable inert ingredients and a lubricant such as magnesium stearate added while mixing. The final mixed granulation is formed into a unit dosage such as a tablet or capsule, as known in the art.

The cooling of the fused granulation can be expedited and result in even more uniform size granules by rapid cooling, as with liquid nitrogen introduced into the stirred granular mixture of PEG and active ingredients. This step reduces manufacturing time and inhibits formation of large granules thus promoting the formation of more uniform sized granules. After cooling, it is preferred to bring the granular mixture to about room temperature for further processing.

In a preferred method, the active ingredients, TT and HCT, are first mixed with a filler and a disintegrating agent such as lactose and sodium starch glycolate for instance, and the like, before mixing with the PEG. Other inert excipients as known in the art of tablet and capsule formulation may be added as determined by the formulator. After mixing with PEG, fusing and formation of granules while cooling, the granular product is mixed with the usual inert excipients, i.e. compacting aids, binders, surfactants, disintegrants, such as microcrystalline cellulose, lactose and sodium starch glycolate, and the like, as known in the tablet and capsule art. A lubricant such as magnesium or calcium stearate, stearic acid, and the like, is mixed with the final granular mixture for its intended purpose.

The following examples, while illustrative of the invention and representing preferred embodiments, are not limiting but serve only to show how the invention may be carried out.

To show the enhanced, optimal, bioavailability of the respective active ingredients of the compositions provided by this invention, tablets were formulated according to this invention containing 75 mg of triamterene and 50 mg of hydrochlorothiazide. Dissolution rate studies were then performed on these tablets using USP Paddle Method in 900 ml of artificial gastric fluid without enzymes, pH 1.2, at 37° C. and at 50 RPM. This test is described under Dissolution, Method II of the 4th Supplement, U.S. Pharmacopeia XIX, National Formulary XIV, page 194, released Jan. 31, 1978; such dissolution results have been utilized by the Food and Drug Administration for triamterene-hydrochlorothiazide combination products (V. P. Shah, F. K. Prassad, J. Lin, G. Knapp, and B. E. Cabana, Biopharmaceutics Laboratory, in a recent paper delivered at the National Meeting of the American Pharmaceutical Association, Academy of Pharmaceutical Sciences Division, Nov. 14-18, 1982). It will be noted that by this dissolution method both the triamterene and the hydrochlorothiazide dissolution rates are excellent for the product made by the present invention.

The following examples utilize PEG 8000 which melts at about 55° C. and is preferred. However, any low melting PEG may be utilized from about PEG-3350 to PEG-20000 to produce the present novel products. It is important to note that the present granules are made of uniform size by milling, screening or grinding, as known in the art, to insure a homogenous product.

EXAMPLES

| Item No. | Ingredients FORMULA: | A | B | C | D |
|---|---|---|---|---|---|
| 1 | Hydrochlorothiazide | 50 | 50 | 50 | 50 |
| 2 | Triamterene | 75 | 75 | 75 | 75 |
| 3 | Lactose - anhydrous - Direct Tablet Grade | 50 | 50 | 50 | 50 |
| 4 | Sodium Starch Glycolate | 10 | 10 | 10 | 10 |
| 5 | Polyethylene Glycol - 8000 | 10 | 20 | 30 | 40 |
| 6 | Microcrystalline Cellulose | 60 | 60 | 60 | 60 |
| 7 | Lactose - anhydrous - Direct Tablet Grade | 123 | 113 | 103 | 93 |
| 8 | Sodium Starch Glycolate | 20 | 20 | 20 | 20 |
| 9 | Magnesium Stearate | 2 | 2 | 2 | 2 |
| | WT. OF A TABLET (mg) | 400 | 400 | 400 | 400 |

Process:

| | |
|---|---|
| Step I | Mix item numbers 1 to 5 in a suitable jacketed blender. |
| Step II | Heat the above with mixing until it fuses (approx. 55° C.). |
| Step III | Cool and pass through a suitable screen to produce uniform size free flowing granules |
| Step IV | Mix granules from Step III with item numbers 6, 7 and 8. Mix to homogeneity. |
| Step V | Add item number 9 and mix as necessary. |
| Step VI | Compress on a suitable tabletting machine or encapsulate on the machine in hard shell capsule. |

Results:

| | Hardness | Disintegration |
|---|---|---|
| Formula A | 9.0 Kg | 4 minutes |
| Formula B | 12.0 Kg | 4 minutes |
| Formula C | Slightly sticky mass | |
| Formula D | Extremely sticky mass - unable to compress | |

| | Observation | Hardness | Disint. Time |
|---|---|---|---|
| Formula A | Granules before compression intermittent flow - may | 9.0 Kg | 4 minutes |

-continued

| | | | |
|---|---|---|---|
| | be acceptable | | |
| Formula B | Free flowing granules | 11.0 Kg | 4 minutes |
| Formula C | Slightly sticky mass | | |
| Formula D | Very sticky mass | | |

From the above results, it is seen that the Formula B is most acceptable and is preferred.

In Table I below, the Dissolution Rates and the Relative Standard Deviation (RSD) of Formula B are compared with those of Maxzide ® tablets, a commercial product marketed by Lederle Laboratories of Pearl River, NY, made by the process of the above Blume et al. patent. In Table II, Formula B is compared with Dyazide ®, marketed by Smith, Kline and French of Philadelphia, PA.

Dissolution Tests

TABLE I

| | Maxzide ® minutes | | | | Formula B (above) minutes | | | |
|---|---|---|---|---|---|---|---|---|
| | 15 | 30 | 45 | 60 | 15 | 30 | 45 | 60 |
| HCT % dissolved | 68.3 | 78.4 | 82.0 | 84.1 | 86.6 | 97.3 | 97.7 | 97.9 |
| RSD: | 7.7 | 4.8 | 4.6 | 5.6 | 7.2 | 3.2 | 2.9 | 2.8 |
| TT % dissolved | 66.7 | 75.7 | 79.1 | 81.5 | 79.8 | 95.5 | 98.5 | 99.7 |
| RSD: | 4.7 | 4.0 | 3.1 | 3.0 | 6.9 | 3.0 | 2.3 | 2.6 |

TABLE II

| | **DYAZIDE ® CAPSULES minutes | | Formula B (above) TABLETS minutes | |
|---|---|---|---|---|
| | 30 | 60 | 30 | 60 |
| HCT % dissolved: | 6.1 | 14.5 | 97.3 | 97.9 |
| RSD: | 2.0 | 1.2 | 3.2 | 2.8 |
| TT % dissolved: | 5.3 | 11.8 | 95.5 | 99.7 |
| RSD: | 1.3 | 1.7 | 3.0 | 2.6 |

**Data reported in Blume et al. patent, above.

The foregoing results show that Formula B in Table I has a good dissolution rate as compared with the presently marketed Maxzide ® tablets. Table II shows significantly better dissolution of the Formula B tablets than presently marketed Dyazide ® capsules.

Table I also shows that the Relative Standard Deviation of both the present Formula B tablets and the prior art Maxzide ® tablets release TT and HCT at a fairly uniform rate.

The granules of Formula B were also encapsulated in hard shell capsules and found to have similar properties as the above tablets.

While the invention has been described with reference to particular embodiments and preferred methods of carrying it out, the invention is not limited to those embodiments but is defined solely by the appended claims.

What is claimed:

1. A method of manufacturing an antihypertensive, diuretic and antihypokalemic pharmaceutical composition comprising the steps of forming a mixture of a PEG, of molecular weight of about 3350 to 20000, a triamterene active pteridine, a hydrochlorothiazide active benzothiadiazide, and an inert filler in which the weight ratio of the pteridine to the benzothiadiazide provides an effective bioavailability of the pteridine to control the hypokalemic condition induced by the dosage amount of the benzothiadiazide and mixing while heating to the melting point of the PEG whereby the mixture instantaneously fuses to form granules, then cooled.

2. A method according to claim 1, wherein the pteridine, the benzothiadiazide, and the filler are mixed with molten, vigorously stirred, polyethylene glycol.

3. A method according to claim 1 or 2, wherein the fused product is rapidly cooled.

4. A method according to claim 1, 2 or 3, wherein the fused product is cooled with liquid nitrogen.

5. A method according to claim 1, wherein the pteridine is triamterene.

6. A method according to claim 5, wherein the benzothiadiazide is hydrochlorothiazide.

7. A method according to claim 6, wherein the triamterene and hydrochlorothiazide are in a clinically effective weight ratio.

8. A method according to claim 7, wherein the clinically effective weight ratio is 1.5:1.

9. A method according to claim 8, wherein said final granulation is formulated into tablets, said tablet formulation containing an additional lubricant mixed therein.

10. A method according to claim 9, wherein the final granulation with lubricant is filled into capsules.

11. A method according to claim 1, wherein lactose is added as the filler together with sodium starch glycolate as a disintegrant.

12. A method according to claim 8 or 9, wherein magnesium stearate is the lubricant.

* * * * *